United States Patent [19]

Bourne

[11] Patent Number: 4,503,560
[45] Date of Patent: Mar. 5, 1985

[54] CHAMOIS HEAD COOLER

[76] Inventor: I. Stanley Bourne, 1900 Sam Bass, Apt. #B11, Denton, Tex. 76205

[21] Appl. No.: 547,257

[22] Filed: Oct. 31, 1983

[51] Int. Cl.³ .................. B65D 30/02; B65D 30/10; B65D 33/16
[52] U.S. Cl. .................................... 383/66; 383/901; 383/907
[58] Field of Search ............. 383/66, 901, 907, 97, 383/102; 128/402, 403; 2/171.2; 62/530

[56] References Cited

U.S. PATENT DOCUMENTS

| | | | |
|---|---|---|---|
| 1,002,021 | 8/1911 | Barnes | 128/402 |
| 1,127,221 | 2/1915 | Finkelstein | 128/402 |
| 1,206,041 | 11/1916 | Slataper | 383/901 |
| 1,322,984 | 11/1919 | Wesley | 128/402 |
| 1,611,877 | 12/1926 | Le Blang | 383/66 |
| 1,927,751 | 9/1933 | Mensi | 383/66 |
| 2,565,394 | 8/1951 | Ryan | 383/66 |
| 2,697,424 | 12/1954 | Hanna | 383/901 |
| 3,011,173 | 12/1961 | Goetz | 383/66 |
| 3,090,045 | 5/1963 | Hurst | 383/901 |
| 3,422,867 | 1/1969 | Wu | 383/66 |
| 4,356,709 | 11/1982 | Alexander | 62/530 |

Primary Examiner—Stephen P. Garbe
Attorney, Agent, or Firm—Michael A. O'Neil

[57] ABSTRACT

A cooling apparatus (10) includes a first sheet (12) and a second sheet (14) both formed from chamois. The sheets are sewn together along a circular line (28) to define an enclosure adapted to receive a quantity of ice (30). The enclosure is provided with an access port (16) which is normally closed either by means of a zipper (20) or by means of a VELCRO closure. In use, the cooling apparatus (10) is placed on the head (32) of a user and is concealed and retained by a cap (34).

3 Claims, 4 Drawing Figures

CHAMOIS HEAD COOLER

TECHNICAL FIELD

This invention relates to apparatus for providing comfort during outdoor or indoor activities, and more particularly to a cooling apparatus that may be utilized during participation in various sport activities.

BACKGROUND AND SUMMARY OF THE INVENTION

The current interest in physical fitness has led to increased participation in outdoor activities by persons of all ages. Certainly the beneficial results deriving from this trend outweigh any disadvantages many times over. It is a fact, however, that excess participation in outdoor activities can cause overheating, resulting in discomfort and sometimes leading to illness.

Various devices, and in particular various types of headgear have heretofore been provided for reducing the possibility of overheating during participation in outdoor activities. For example, many people wear a cap while out of doors in order to reduce the exposure of the head to the sun. It has been found that such a cap does not always provide adequate protection and that in some instances additional steps must be taken in order to insure against overheating.

The present invention relates to cooling apparatus which is highly adapted for use during participation in outdoor or indoor activities, and in particular to use during participation in various sports, etc. The use of the invention is advantageous in that apparatus constructed in accordance therewith may be used unobtrusively. Another advantage in the use of the invention relates to the fact that apparatus constructed in accordance therewith is both highly economical to purchase and adapted for long term service.

In accordance with the broader aspects of the invention, a cooling apparatus comprises a chamois container adapted to receive and contain a quantity of ice, preferably in the form of small ice cubes or crushed ice. The container is dimensioned to be placed on top of the head and to be received within a typical sports cap, whereby the container is entirely hidden from view during use. The chamois construction of the container is highly advantageous in that it protects the user against discomfort resulting from direct contact with the ice, while at the same time entirely containing the water that results from the melting of the ice.

In accordance with more specific aspects of the invention, the container comprises a first generally circular sheet of chamois which is gathered to provide a generally flat bottom wall and an annular partial top wall. A second generally circular sheet of chamois is smaller in diameter than the first sheet and is secured to the periphery of the first sheet to close the top wall of the container. The second sheet of chamois is provided with an access port which is normally closed by means of a zipper or other suitable closure means.

DESCRIPTION OF THE DRAWINGS

A more complete understanding of the invention may be had by reference to the following Detailed Description when taken in conjunction with the accompanying Drawings wherein.

DETAILED DESCRIPTION

Figure 1:
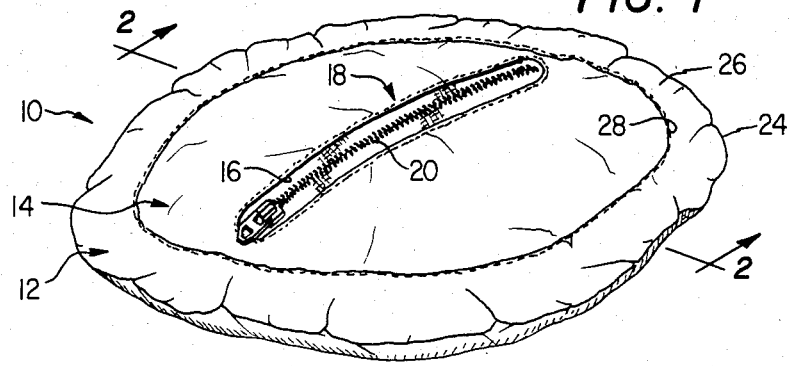
FIG. 1 is a top view of the cooling apparatus incorporating a first embodiment of the invention.

Referring now to the Drawing, and in particularly to FIG. 1 thereof, there is shown a cooling apparatus 10 incorporating a first embodiment of the invention. The cooling apparatus 10 comprises a first sheet 12 which is preferrably formed from chamois. The first chamois sheet 12 is circular in configuration and is characterized by relatively large diameter. A second sheet 14 is also formed from chamois. The second chamois sheet 14 is also generally circular in configuration and is characterized by a relatively small diameter. The second sheet 14 includes an access port 16 which is normally closed by means of suitable closure apparatus 18. In accordance with the first embodiment of the invention the closure apparatus 18 comprises a zipper 20.

Figure 2:
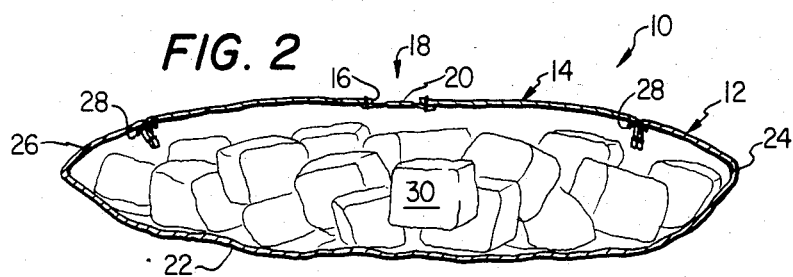
FIG. 2 is a sectional view taken generally along the line 2—2 in FIG. 1.

Referring to FIGS. 1 and 2, the first chamois sheet 12 defines a relatively flat bottom wall 22 extending to a generally circular outer edge 24 and an annular partial top wall 26 extending inwardly from the edge 24. It will be understood that the first chamois sheet 12 comprises an initially flat sheet which is folded annularly inwardly and gathered to define the edge 24 and the partial top wall 26.

The second chamois sheet 14 has a circular periphery which is sewn to the periphery of the first chamois sheet 12 along a line of stitching 28. The access port 16 preferrably comprises a diagonally extending slit. The slit is normally closed by the closure structure 18 comprising the zipper 20 which is sewn in place.

Figure 4:
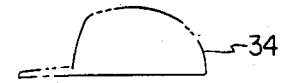
FIG. 4 is an illustration of the use of the invention.
Figure 4:
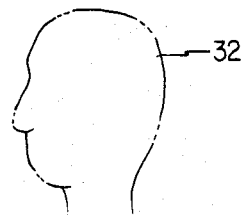

FIGS. 2 and 4 illustrate the use of the cooling apparatus 10. A quantity of ice 30 is initially admitted to the interior of the cooling apparatus 10. This is accomplished by opening the zipper 20, and then directing ice into the interior of the cooling apparatus 10 through the access port 16. The ice is preferably either in the form of small cubes or crushed ice, however, any available form of ice may be utilized in the practice of the invention. After a sufficient quantity of ice has been received within the cooling apparatus 10, the access port 16 is closed by means of the zipper 20.

Referring specifically to FIG. 4, the cooling apparatus 10 is placed on the top of the head 32 of the user. The cooling apparatus 10 is preferably contained and concealed by means of a cap 34 which is positioned on the head 32 of the user over the cooling apparatus 10. The cap 34 retains the cooling apparatus 10 sufficiently to permit the user to engage in a wide variety of sports activities while the cooling apparatus 10 is in use.

The use of chamois in construction of the cooling apparatus 10 comprises an important feature of the invention. Chamois has thermal insulating properties, whereby the use of chamois in the construction of the cooling apparatus 10 prevents overcooling, which would lead to discomfort. Likewise, because of its nature, the chamois serves to retain water which results from the melting of the ice. Thus, the cooling apparatus 10 continues to function due to the positioning of the wet chamois material on the head of the user even after the ice is entirely melted.

Figure 3:
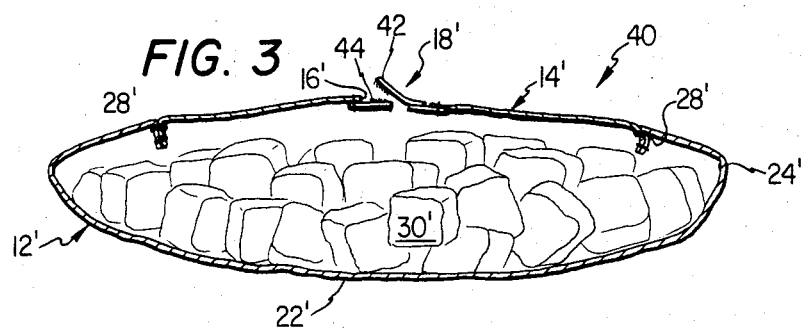
FIG. 3 is a view similar to FIG. 2 illustrating a second embodiment of the invention.

FIG. 3 illustrates the cooling apparatus 40 comprising a second embodiment of the invention. The cooling apparatus 40 of FIG. 3 incorporate numerous component parts which are substantially identical in construction and function to component parts of the cooling apparatus 10 illustrated in FIGS. 1 and 2 and described hereinabove in conjunction therewith. Such identical component parts are designated in FIG. 3 with the same reference numerals utilized in the description of the cooling apparatus 10, but are differentiated therefrom by means of a prime (') designation.

The primary distinction between the cooling apparatus 40 and the cooling apparatus 10 involves the fact that the cooling apparatus 40 utilizes a closure apparatus 18' of the type sold under the trademark VELCRO. Such a closure apparatus includes a fabric layer 42 comprising a multiplicity of hooks which is secured to one side of the access port 16', and a fabric layer 44 comprising a multiplicity of loops which is secured to the opposite side. Such a closure apparatus 18' is easily utilized by simply pressing the two fabric layers into engagement with one another.

It will thus be understood that the present invention comprises a cooling apparatus which is readily adapted for use in conjunction with various outdoor activities, particularly including sports activities. The cooling apparatus of the invention is advantageous in that it is economical to manufacture and is adapted for long term service. Another important feature of the invention involves the fact that cooling apparatus constructed in accordance therewith is highly unobtrusive in use.

Although preferred embodiments of the invention have been illustrated in the accompanied Drawing and described in the foregoing Detailed Description, it will be understood that the invention is not limited to the embodiments disclosed but is capable of numerous rearrangements, modifications, and substitutions of parts and elements without departing from the spirit of the invention.

I claim:

1. A cooling apparatus comprising:
   a first sheet formed from chamois having a substantially circular shape and characterized by a relatively large diameter;
   said first sheet being gathered to define a substantially flat bottom wall extending to a substantially circular rim and an annular partial top wall extending inwardly from the circular rim;
   a second sheet formed from chamois having a substantially circular shape and characterized by a relatively small diameter;
   the periphery of the second sheet being sewn to the periphery of the first sheet along a circular line to complete the top wall of the apparatus;
   said second sheet having an access port formed therein; and
   closure means for normally closing the access port of the second sheet.

2. The cooling apparatus according to claim 1 wherein the closure means comprises a zipper.

3. The cooling apparatus according to claim 1 wherein the closure means comprises a VELCRO closure.

* * * * *